US010352837B2

United States Patent
Shaw et al.

(10) Patent No.: US 10,352,837 B2
(45) Date of Patent: Jul. 16, 2019

(54) OPTOMECHANICAL REFERENCE

(71) Applicant: The United States of America, as represented by the Secretary of Commerce, Washington, DC (US)

(72) Inventors: Gordon Shaw, Takoma Park, MD (US); Jacob Taylor, Washington, DC (US); Ryan Wagner, Gaithersburg, MD (US); Felipe Guzman, Bremen (DE)

(73) Assignee: THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 0 days.

(21) Appl. No.: 15/850,396

(22) Filed: Dec. 21, 2017

(65) Prior Publication Data

US 2019/0033187 A1   Jan. 31, 2019

Related U.S. Application Data

(60) Provisional application No. 62/536,713, filed on Jul. 25, 2017.

(51) Int. Cl.
*G01N 3/02* (2006.01)
*G01G 3/08* (2006.01)
*G02B 17/00* (2006.01)
*G01L 1/04* (2006.01)

(52) U.S. Cl.
CPC ............... *G01N 3/02* (2013.01); *G01G 3/08* (2013.01); *G01L 1/044* (2013.01); *G02B 17/004* (2013.01); *G01N 2203/029* (2013.01)

(58) Field of Classification Search
CPC . G01N 3/02; G01G 3/08; G01L 1/044; G02B 17/004
See application file for complete search history.

(56) References Cited

U.S. PATENT DOCUMENTS

| 9,625,313 | B2* | 4/2017 | Lehman | ..................... G01J 1/56 |
| 2017/0371065 | A1* | 12/2017 | Guzman | ................. G01P 21/00 |
| 2017/0373462 | A1* | 12/2017 | Guzman | ............... H01S 5/0602 |

OTHER PUBLICATIONS

Melcher, J., et al., A self-calibrating optomechanical force sensor with femtonewton resolution, Applied Physics Letters, 2014, 105.

* cited by examiner

*Primary Examiner* — Jamel E Williams
(74) *Attorney, Agent, or Firm* — Office of Chief Counsel for National Institute of Standards and Technology

(57) ABSTRACT

An optomechanical reference includes a basal member; a flexure that includes: a floating link; a first flexural member; and a second flexural member such that: the floating link is moveably disposed; a first stator; a second stator; a first cavity including: a first primary mirror; a first secondary mirror; a first optical coupler in optical communication with the first secondary mirror; and a first cavity length; and a second cavity including: a second primary mirror; a second secondary mirror; a second optical coupler; and a second cavity length.

13 Claims, 14 Drawing Sheets

OPTOMECHANICAL REFERENCE

CROSS REFERENCE TO RELATED APPLICATIONS

This application claims the benefit of U.S. Provisional Patent Application Ser. No. 62/536,713, filed Jul. 25, 2017, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce, and under Agreement No. 70NANB11H125 awarded by The University of Maryland. The Government has certain rights in the invention. Licensing inquiries may be directed to the Technology Partnerships Office, NIST, Gaithersburg, Md., 20899; voice (301) 301-975-2573; email tpo@nist.gov; reference NIST Docket Number 17-016US1.

BRIEF DESCRIPTION

Disclosed is an optomechanical reference comprising: a basal member; a flexure disposed on the basal member and comprising: a floating link disposed on the basal member; a first flexural member interposed between the basal member and the floating link; and a second flexural member interposed between the basal member and the floating link such that: the floating link is moveably disposed on the basal member via flexing of the first flexural member and the second flexural member, and the first flexural member and the second flexural member are spaced apart and in mechanical communication by the floating link; a first stator disposed on the basal member and opposing the flexure such that: the first stator is spaced apart from the flexure, and the first stator is subject to displacement when the basal member is displaced; a second stator disposed on the basal member and opposing the flexure such that: the second stator is spaced apart from the flexure, and the second stator is subject to displacement when the basal member is displaced; a first cavity comprising: a first primary mirror disposed on the flexure; a first secondary mirror disposed on the first stator and in optical communication with the first primary mirror; a first optical coupler in optical communication with the first secondary mirror and that provides a first laser light to the first cavity; and a first cavity length comprising a first distance between the first primary mirror and the first secondary mirror; and a second cavity comprising: a second primary mirror disposed on the flexure; a second secondary mirror disposed on the second stator and in optical communication with the second primary mirror; a second optical coupler in optical communication with the first secondary mirror and that provides a second laser light to the second cavity; and a second cavity length comprising a second distance between the second primary mirror and the second secondary mirror.

Also disclosed is a process for performing optomechanical reference metrology, the process comprising: providing an optomechanical reference; receiving the first laser light by the first cavity; reflecting the first laser light between the first primary mirror and the first secondary mirror of the first cavity; flexing the flexure with respect to the first stator in response to the reflecting the first laser light; producing first reference light by the first cavity; receiving the second laser light by the second cavity; reflecting the second laser light between the second primary mirror and the second secondary mirror of the second cavity; flexing the flexure with respect to the second stator in response to the reflecting the second laser light; and producing second reference light by the second cavity to perform optomechanical reference metrology.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered an optomechanical reference provides a mechanical sensor such that the photon pressure force resulting from the reflection of light can be amplified using an optical cavity and used to drive the motion of the mechanical sensor. The optomechanical reference can be used as a calibration reference for mass or force where the calibration comes from a measurement of laser power circulating in the optical cavity. An additional optical cavity can be used to transduce motion of a force sensor simultaneously. The measurement has a built-in cross-check from thermomechanical vibration of the force sensor, which continuously monitors and evaluates quality of the calibration. Properties of the optical cavity can be tuned, e.g., by varying a wavelength of light received by the optical cavity or by changing a length of the optical cavity. The wavelength can lock the cavity in an optical resonance.

Figure 1:
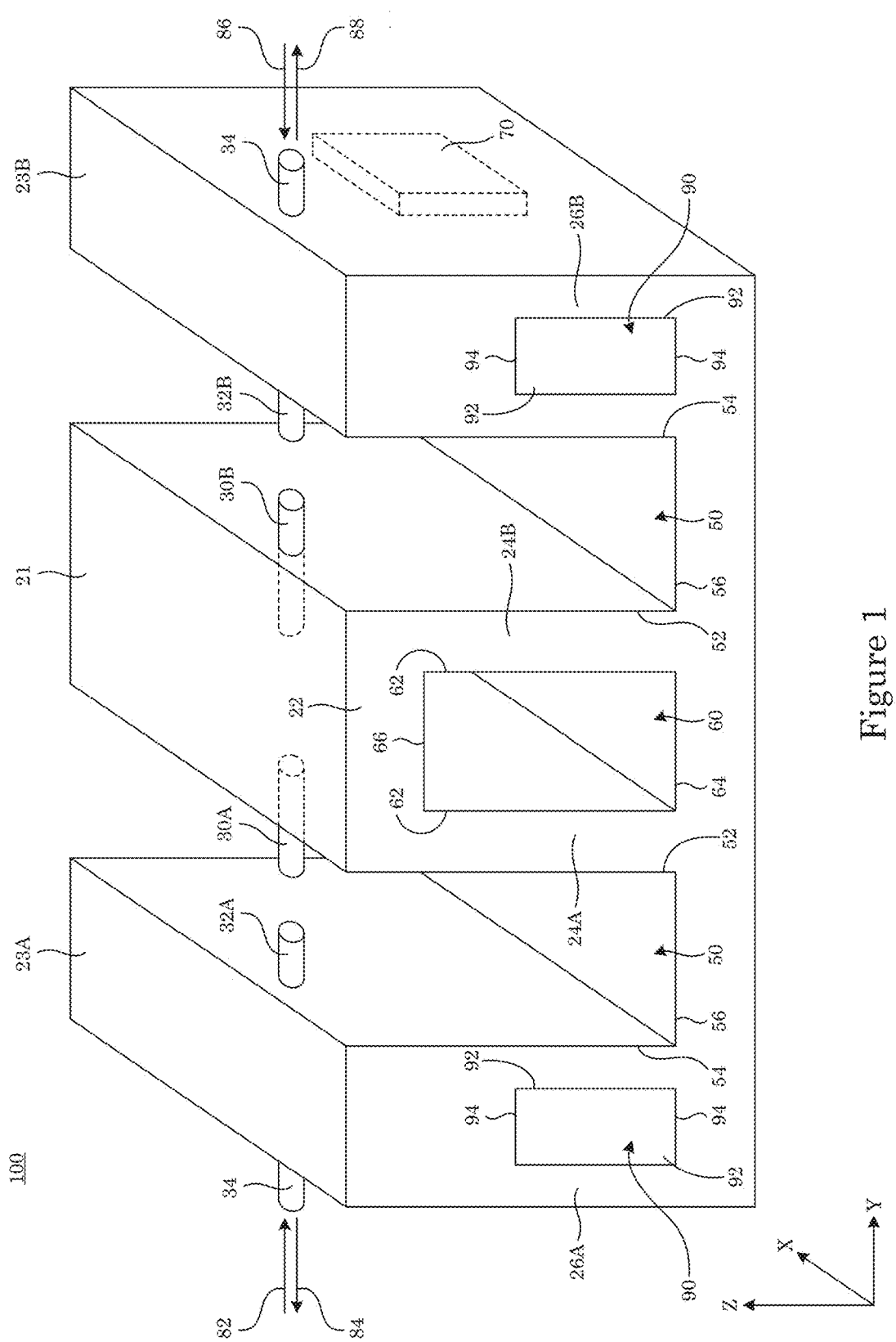
FIG. 1 shows a perspective view of an optomechanical reference.
Figure 2:
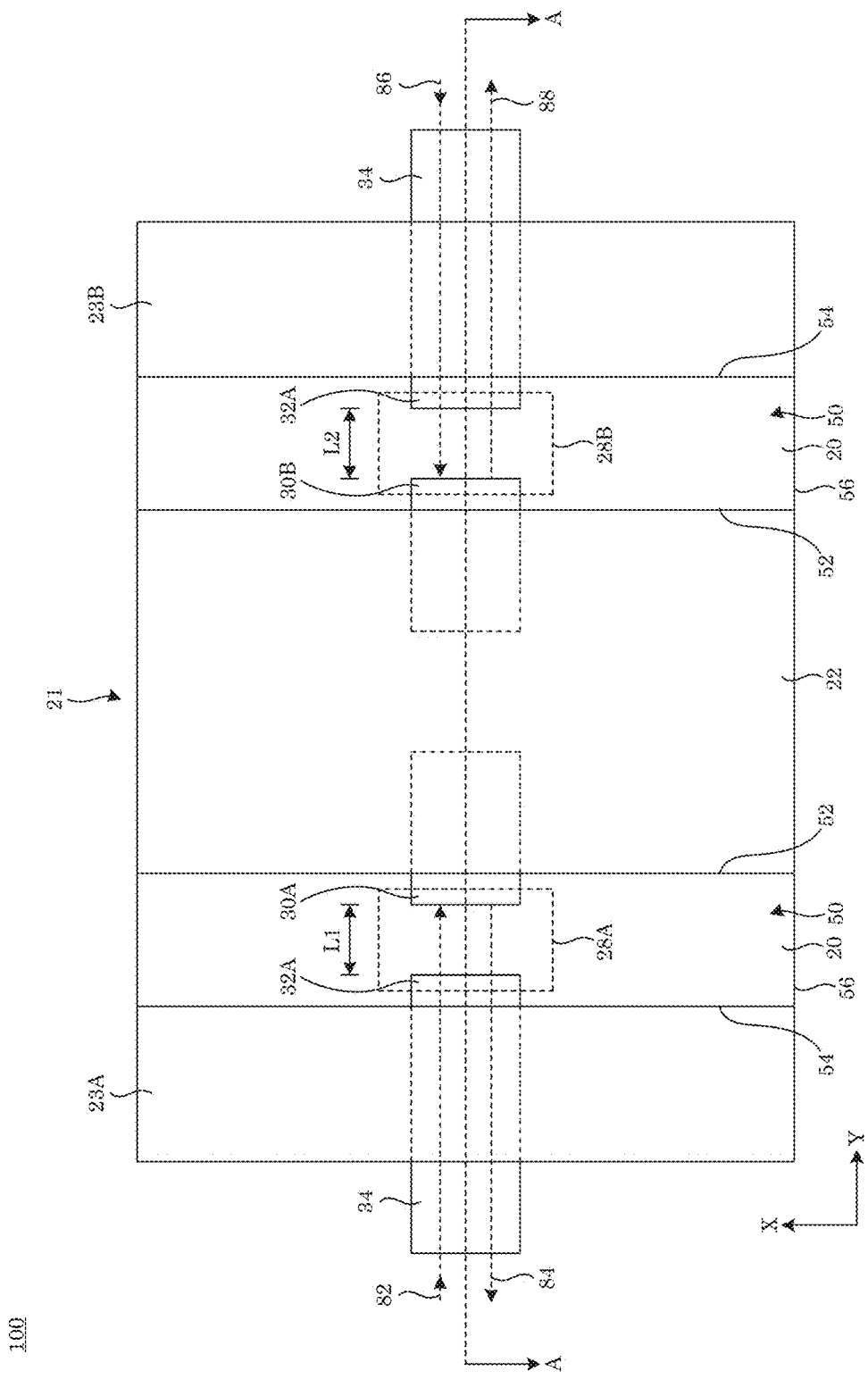
FIG. 2 shows a top view of the optomechanical reference show in FIG. 1.
Figure 3:
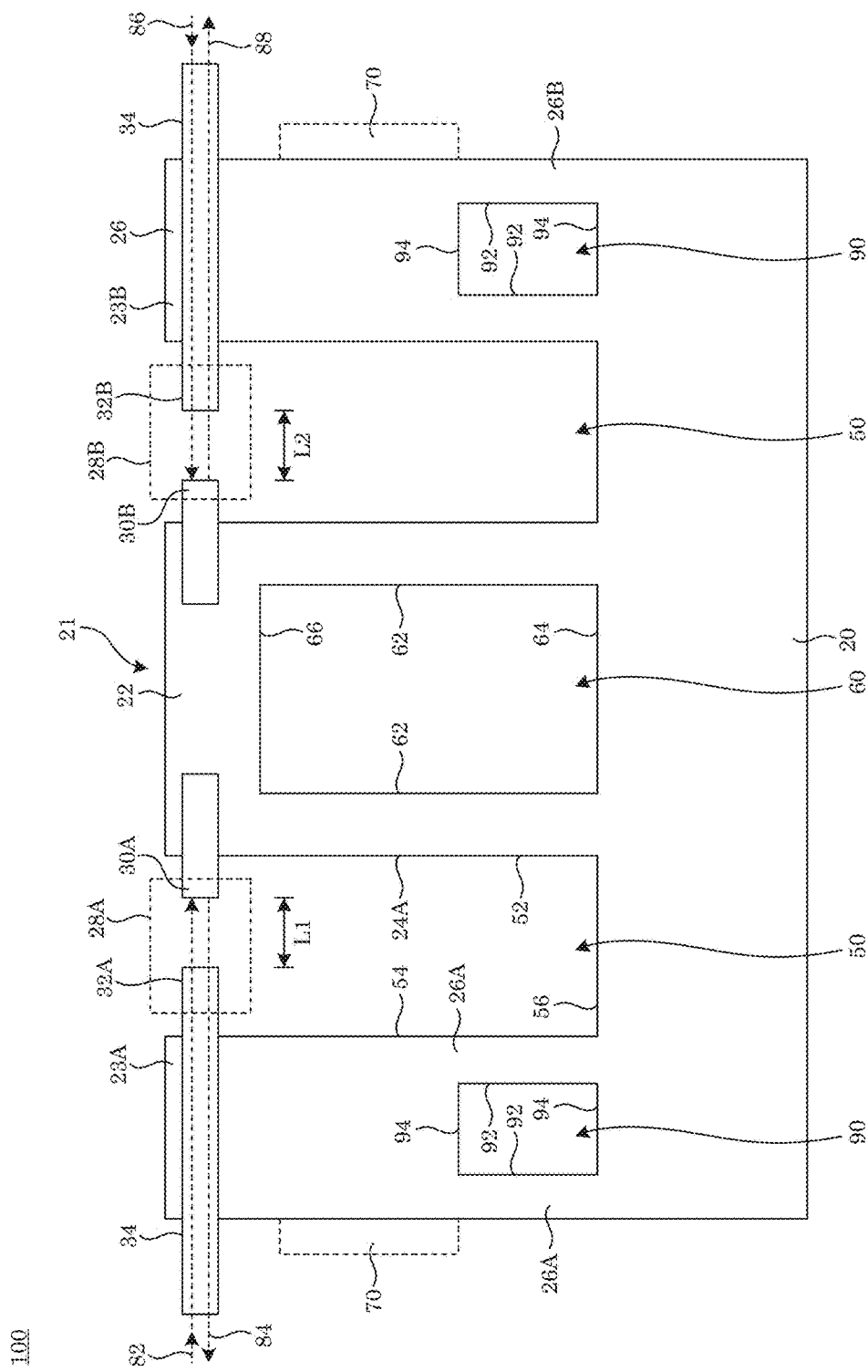
FIG. 3 shows a cross-section along line A-A of the optomechanical reference shown in FIG. 2.

In an embodiment, with reference to FIG. 1, FIG. 2, and FIG. 3, optomechanical reference 100 includes basal member 20; flexure 21 disposed on basal member 20. Flexure 21 includes floating link 22 disposed on basal member 20; first flexural member 24A interposed between basal member 20 and floating link 22; and second flexural member 24B interposed between basal member 20 and floating link 22, wherein floating link 22 is moveably disposed on basal member 20 via flexing of first flexural member 24A and second flexural member 24B, and first flexural member 24A and second flexural member 24B are spaced apart and in mechanical communication by floating link 22. Optomechanical reference 100 also includes first stator 23A disposed on basal member 20 and opposing flexure 21, wherein first stator 23A is spaced apart from flexure 21, and first stator 23A is subject to displacement when basal member 20 is displaced. Second stator 23B is disposed on basal member 20 and opposes flexure 21, wherein second stator 23B is spaced apart from flexure 21, and second stator 23B is subject to displacement when basal member 20 is displaced. Optomechanical reference 100 further includes first cavity 28A that includes: first primary mirror 30A disposed on flexure 21; first secondary mirror 32A disposed on first stator 23A and in optical communication with first primary mirror 30A; first optical coupler 34 in optical communication with first secondary mirror 32A and that provides first laser light 82 to first cavity 28A; and first cavity length L1 that is a first distance between first primary mirror 30A and first secondary mirror 32A. Second cavity 28B of optomechanical reference 100 includes: second primary mirror 30B disposed on flexure 21; second secondary mirror 32B disposed on second stator 23B and in optical communication with second primary mirror 30A; second optical coupler 34 in optical communication with first secondary mirror 32B and that provides second laser light 86 to second cavity 28B; and second cavity length L2 that is a second distance between second primary mirror 30B and second secondary mirror 32B. Here, first cavity 28A receives first laser light 82 via optical coupler 34 and produces first reference light 84 from first laser light 82. Additionally, second cavity 28B receives second laser light 86 via optical coupler 34 in optical communication with second cavity 28B and produces second reference light 86 from second laser light 84.

First armature 26A can be disposed on basal member 20, wherein first stator 23A is disposed on first armature 26A. Optomechanical reference 100 can include second armature 26B disposed on basal member 20, wherein second stator 23B is disposed on second armature 26B. Here, flexure 21 is interposed between first stator 23A and second stator 23B. Gap 50 separates flexure 21 from first stator 23A and also from second stator 23B. Gap 50 is bounded by walls (52, 54, 56). Stator 23 (e.g., 23A, 23B) can include gap 90 that is bounded by walls (92, 94).

Stator 21 includes floating link 22 disposed on flexural members (24A, 24B) with gap 60 bounded by walls (62, 64, 66).

In some embodiments, optomechanical reference 100 includes piezoelectric member 70. Piezoelectric member 70 can be disposed on first stator 23A, second stator 23B, or a combination thereof. Piezoelectric member 70 receives a voltage and dynamically adjusts optical cavity length L (e.g., L1, L2) to maintain an optical resonance of cavity 28 (e.g., 28A, 28B) and to produce a proportional voltage signal that corresponds to changes to cavity length L, which can be used for control or readout. Accordingly, piezoelectric member 70 provides selectively adjusts gap 50 such that an optical resonance of cavity 28 can be maintained and diagnostic information provided.

Figure 4:
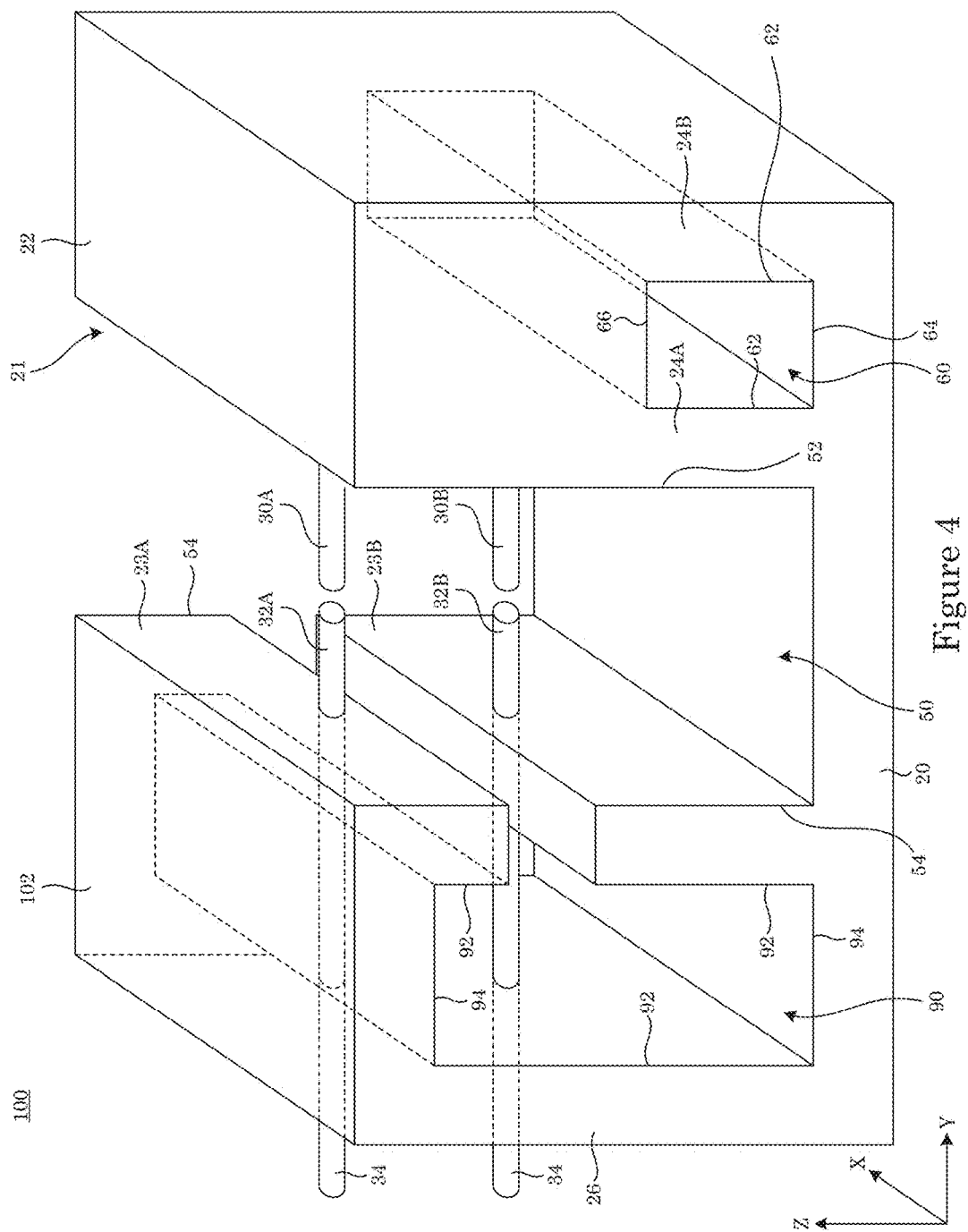
FIG. 4 shows an optomechanical reference.
Figure 5:
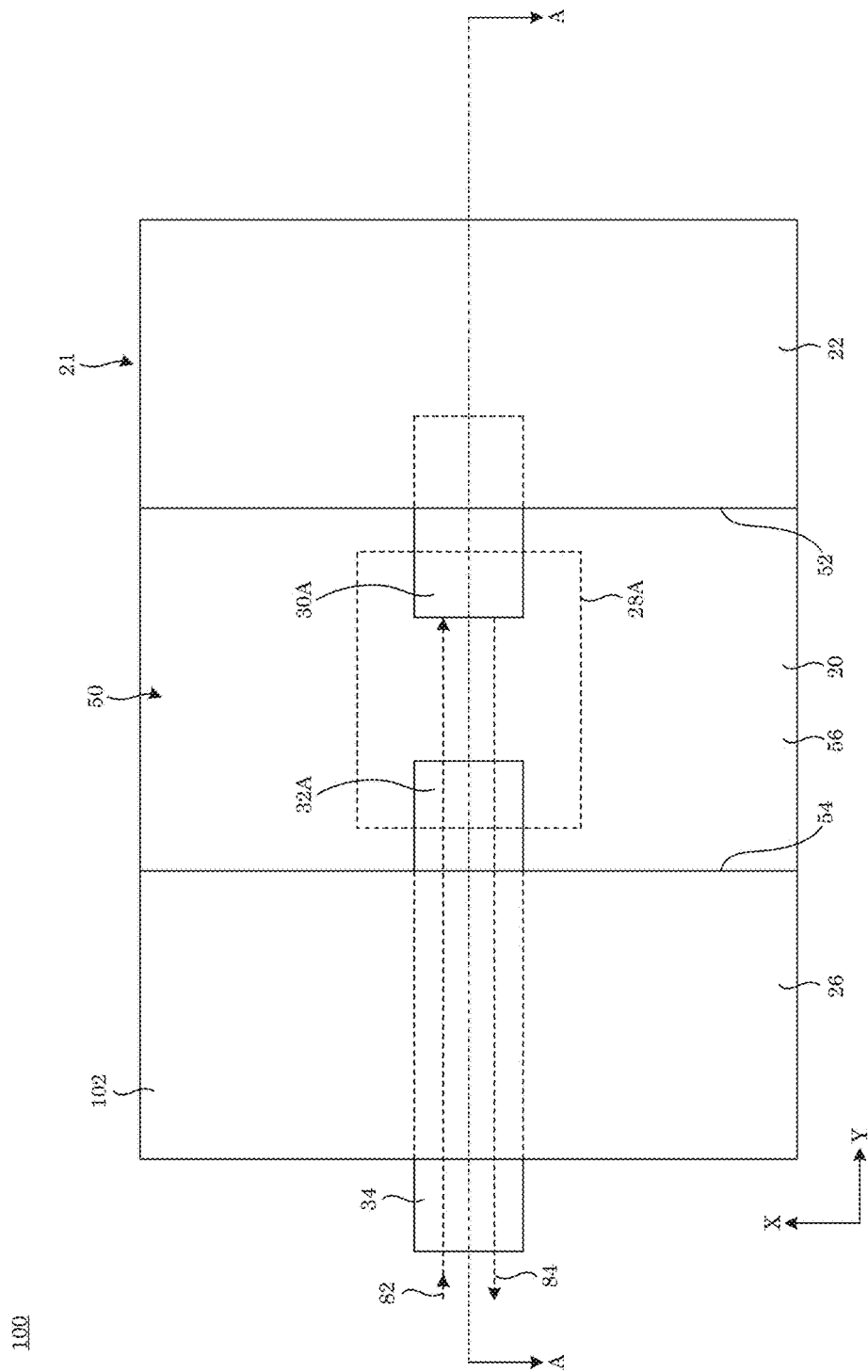
FIG. 5 shows a top view of the optomechanical reference shown in FIG. 4.
Figure 6:
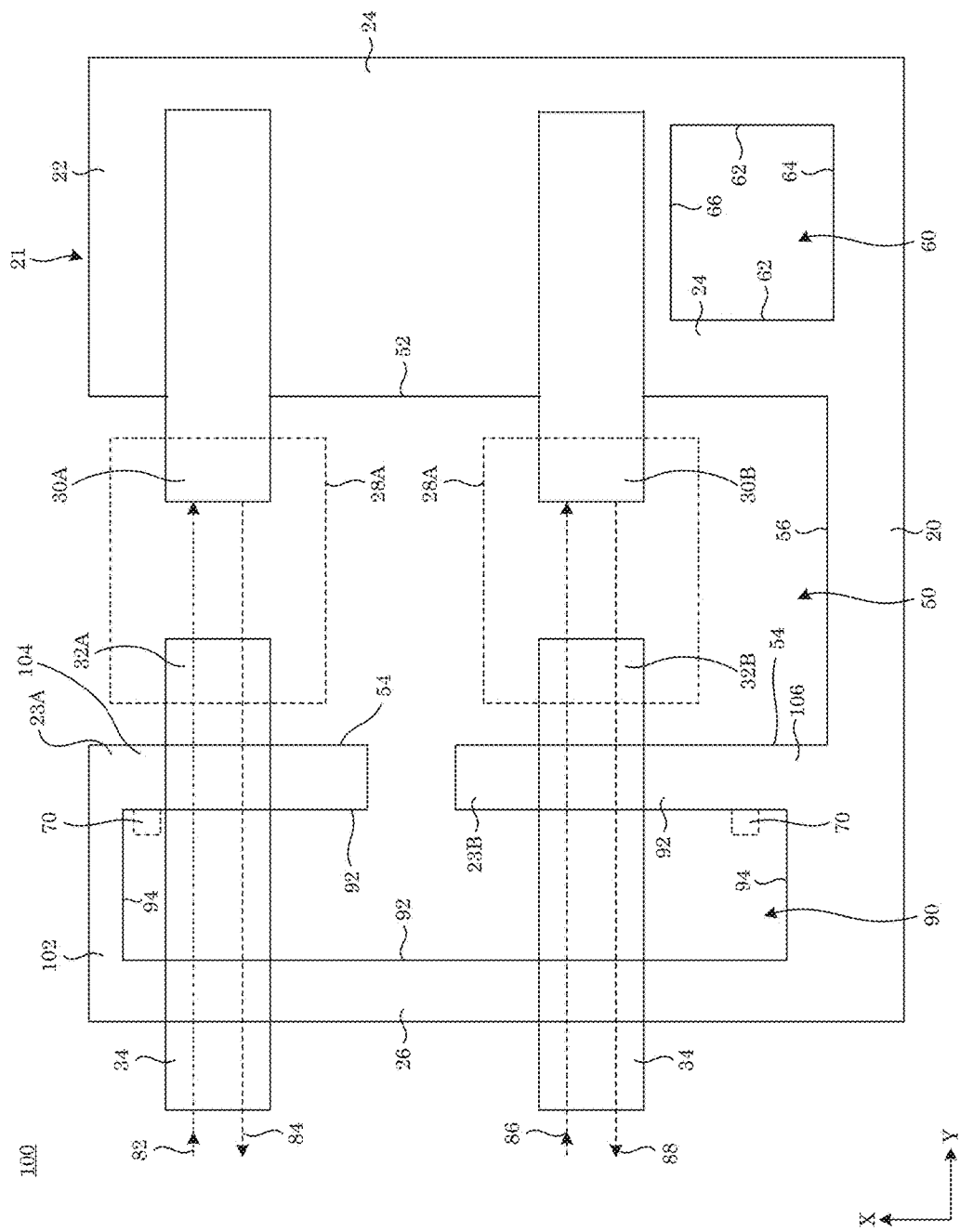
FIG. 6 shows a cross-section along line A-A of the optomechanical reference shown in FIG. 5.

In an embodiment, with reference to FIG. 4, FIG. 5, and FIG. 6, optomechanical reference 100 includes armature 26 disposed on basal member 20, wherein first stator 23A and second stator 23B are disposed on armature 26. Here, arm 102 attaches stator 23A to armature 26 with second stator 23B disposed on basal member 20 such that first primary mirror 32A and second primary mirror 32B are disposed opposing a same surface of flexure 21, and first primary mirror 30A and second primary mirror 30B are disposed on the same surface of flexure 21.

It is contemplated that armature 26 and flexural member 24 are spaced apart by gap 50 bounded by walls (52, 54, 56). Similarly, flexural members (24A, 24B) are separated by gap 60 bounded by walls (62, 64). Gap 60 can be from 1 micrometer to 1 meter, specifically from 1 micrometer to 10 centimeters. Further, cavity length L (e.g., L1, L2) can be from 1 micrometer to 1 meter, specifically from 1 micrometer to 10 centimeters. Gap 50 can be from 1 micrometer to 1 meter, specifically from 1 micrometer to 10 centimeters.

Flexural member 24 can be a leaf spring that has an anisotropic aspect ratio with respect to dimensions of its thicknesses. Here, flexural member 24 can have first thickness T1 from 10 nanometers to 10 centimeters, specifically from 1 micrometer to 1 centimeter. Additionally, flexural member 24 can have second thickness T2, at least 8 times larger than T1, from 80 nm to 80 centimeters, specifically from 8 micrometers to 8 centimeters.

Dimensions of optomechanical reference 100 can include first width W1 and second width W2 independently from 10 nanometers to 10 centimeters, specifically from 1 micrometer to 1 centimeter. Moreover, floating link 22 can have width W3 from 10 nanometers to 10 centimeters, specifically from 1 micrometer to 1 centimeter.

In optomechanical reference 100, floating link 22 can include a material selected for disposition of primary mirror 30 thereon. Exemplary materials for floating link 22 include a metal, polymer, glass, ceramic, semiconductor, metalloid, main group element, non-metal element, an electrical insulator, an electrical conductor, and the like, or a combination thereof. In an embodiment, floating link 22 includes silica. A mass of floating link 22 can depend on a material property (e.g., a density) and can be, e.g., from 100 milligrams (mg) to 100 g.

In optomechanical reference 100, floating link 22 is disposed on flexural member 24. Flexural member 24 provides a restoring force to floating link 22 relative to basal member 20 and provides a uniaxial response of displacement to acceleration. First cavity 28A has first cavity length L1 with flexural members (24A, 24B) at a non-flexed rest position, and first cavity length L1 changes when flexural members (24A, 24B) move relative to first stator 23A. Similarly, second cavity 28B has second cavity length L2 with flexural members (24A, 24B) at a non-flexed rest position, and second cavity length L2 changes when flexural members (24A, 24B) move relative to second stator 23B. In this regard, first cavity length L1 and second cavity length L2 independently can be from 1 micrometer to 1 meter, specifically from 10 micrometers to 1 centimeter.

Flexural member 24 can include a material so that flexural member 24 has a Young's modulus to provide a selected amplitude of displacement of floating link 22 relative to armature 26. The Young's modulus of flexural member 24 can be from 0.01 to 1050 GPa, from 10 to 500 specifically. Exemplary materials for flexural member 24 include a metal, polymer, glass, ceramic, semiconductor, metalloid, main group element, non-metal element, an electrical insulator, an electrical conductor, and the like, or a combination thereof. Flexural member 24 can be a same or different material then that of floating link 22. In an embodiment, flexural member 24 includes silica. A mass of flexural member 24 can be from 1 picogram to 100 kg, from 1 microgram to 100 grams, specifically.

In optomechanical reference 100, floating link 22, flexural member 24, and armature 26 are disposed on basal member 20. Basal member 20 provides a reference position to compare to a position of floating link 22. It is contemplated that basal member 20 can include a material selected for rigidity of coupling of stator 23 (e.g., 23A, 23B) and flexure 21. Exemplary materials for basal member 20 include a metal, polymer, glass, ceramic, semiconductor, metalloid, main group element, non-metal element, an electrical insulator, an electrical conductor, and the like, or a combination thereof. In an embodiment, basal member 20 includes silica. A mass of basal member 20 can be from a mass of floating link 22 to up to 100 times the mass of floating link 22.

Displacement of floating link 22 changes cavity length L (e.g., L1, L2) of cavity 28 (e.g., 28A, 28B). In optomechanical reference 100, primary mirror 30 provides a reference point for reflected light and estimates the position of floating link 22. It is contemplated that primary mirror 30 can include a material selected for reflection of laser light therefrom. Exemplary materials for primary mirror 30 include fused-silica, quartz, a lithium-aluminosilicate glass-ceramic (e.g., commercially available under trademark ZERODUR), a glass ceramic, and the like, or a combination thereof. In an embodiment, primary mirror 30 is formed on a laser-ablated surface of an optical mirror and then coated with a high-reflectivity dielectric mirror or a moderate reflectivity metal surface. Further, primary mirror 30 can be concave for alignment of laser light into cavity 28.

Secondary mirror 32 receives laser light (e.g., 82, 86) from an external light source via optical coupler 34 and communicates the laser light to primary mirror 30 as part of cavity 28. In this manner, secondary mirror 32 in combination with primary mirror 30 provides an optical cavity whose length L is determined in part by the position of floating link 22. It is contemplated that secondary mirror 32 can include a material selected for communication of laser light therethrough. Exemplary materials for secondary mirror 32 can be a same material as primary mirror 30, and the like, or a combination thereof. In an embodiment, secondary mirror 32 includes the same material as that of primary mirror 30. Secondary mirror can be planar with a lower reflectivity than primary mirror 30.

Optical coupler 34 provides laser light to cavity 28 through secondary mirror 32. In an embodiment, optical coupler 34 and secondary mirror 28 is a monolithic, same optical element. In some embodiments, optical coupler 34 and secondary mirror 28 are different discrete optical elements that are in optical communication and that can be in mechanical communication. Exemplary materials for optical coupler 34 can be a same material as secondary mirror 32, and the like, or a combination thereof. In an embodiment, optical coupler 34 is a fiber optical fiber.

In an embodiment, arm 102 (see. e.g., FIG. 4) extends from armature 26 and separates armature 26 from first stator 23A. Arm 102 can be a same material as armature 26, basal member 20, or a combination thereof.

Cavity 28 that includes primary mirror 30 and secondary mirror 32 optically connects the position of floating link 22 and a resonant wavelength of cavity 28. Cavity 28 can have a free spectral range from 5 to 1000 THz from 0.5 to 500 THz. The wavelength of laser light communicated in cavity 28 can be from 15 nm to 20.0 μm, specifically from 0.6 μm to 1.7 μm.

Figure 7:
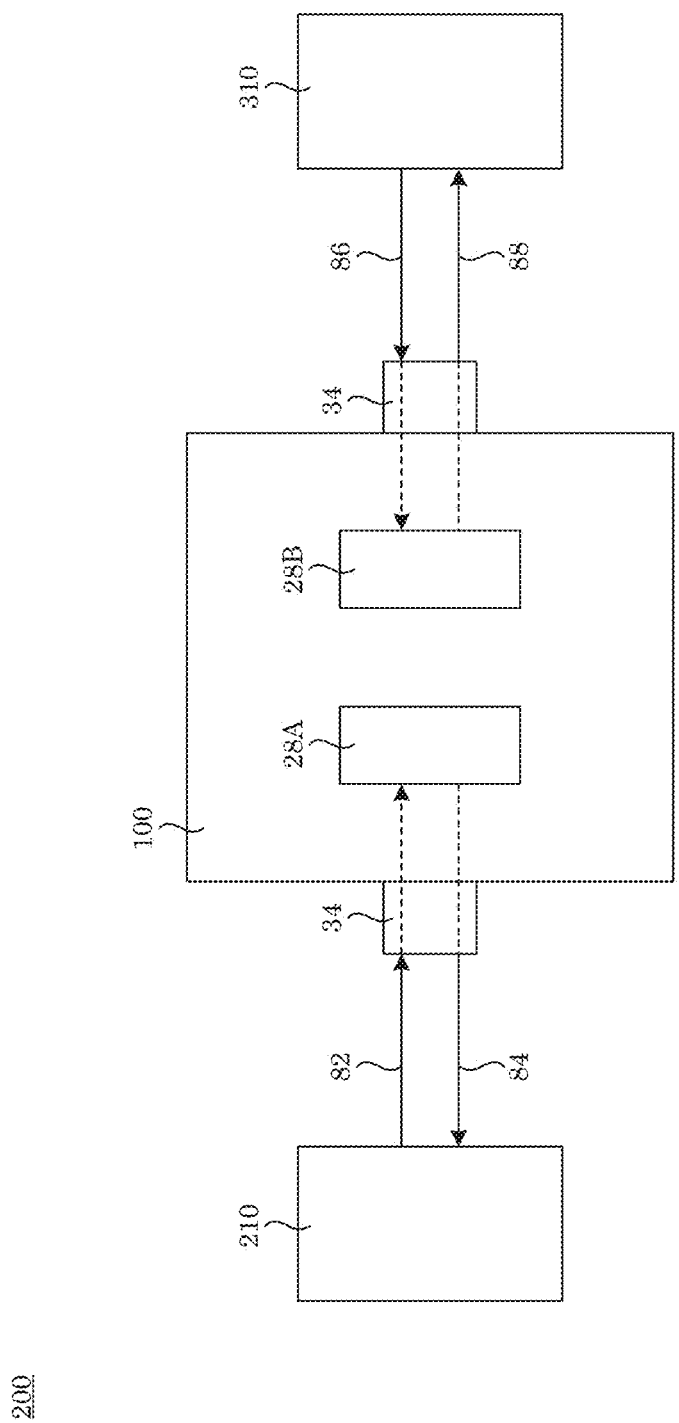
FIG. 7 shows a reference system that includes an optomechanical reference.
Figure 8:
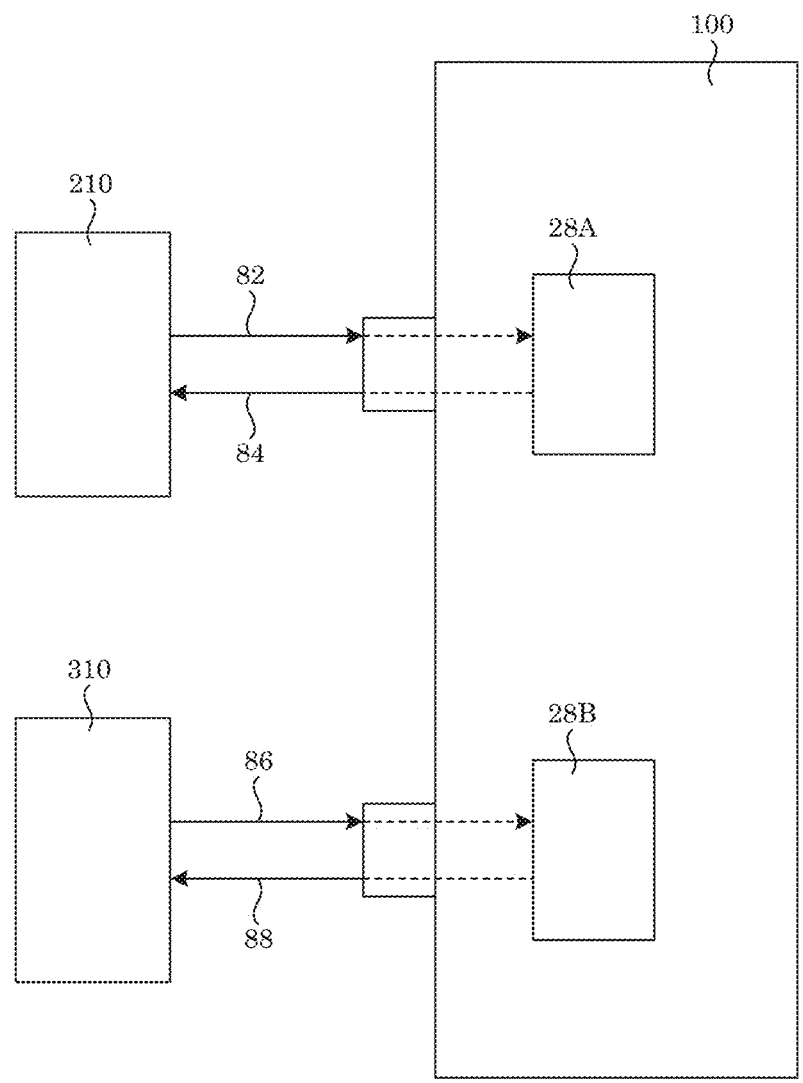
FIG. 8 shows a reference system that includes an optomechanical reference.

In an embodiment, with reference to FIG. 7 and FIG. 8, optomechanical reference 100 receives first laser light 82 from first light member 210; communicates first reference light 84 to first light member 210; receives second laser light 86 from second light member 310; and communicates second reference light 88 to second light member 310.

Figure 9:
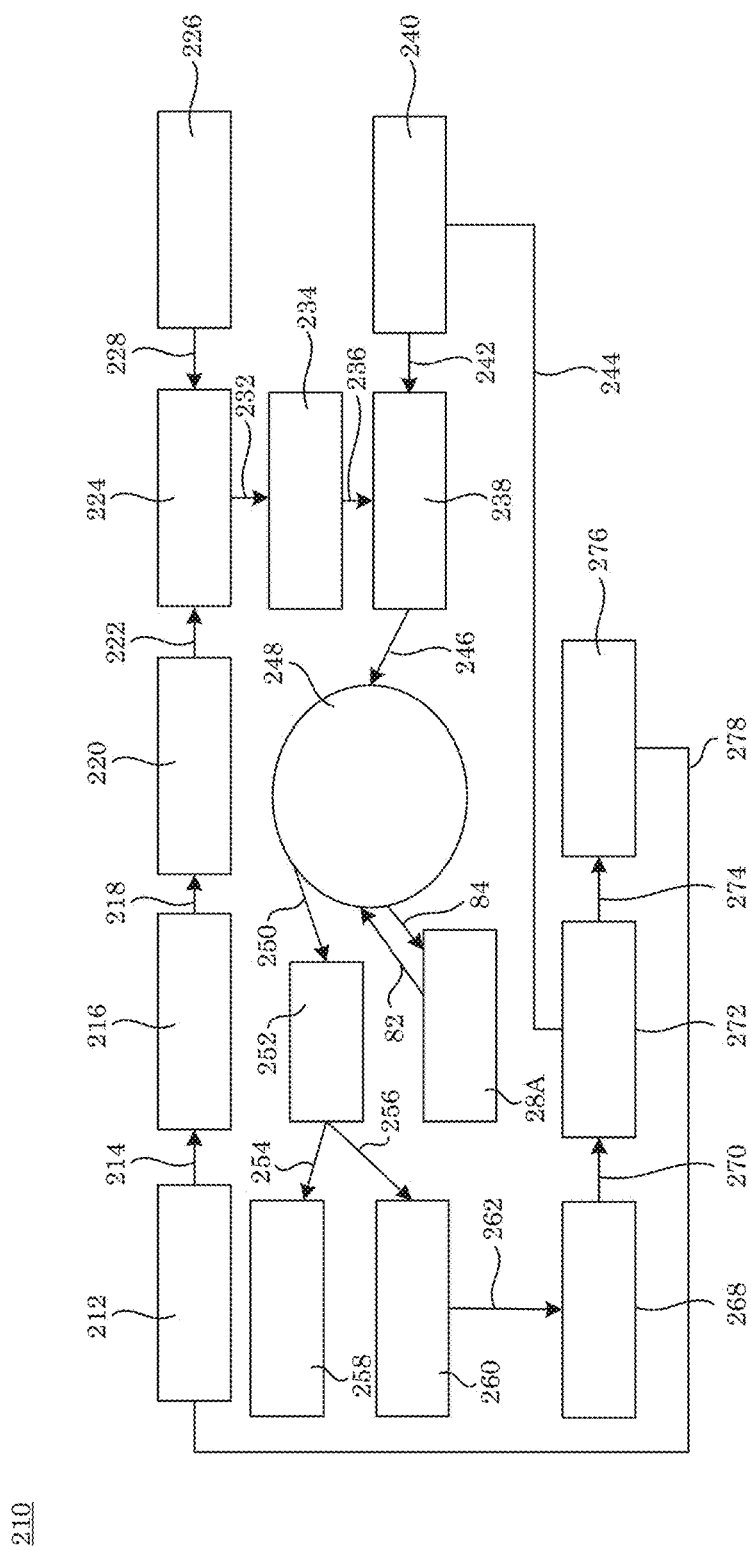
FIG. 9 shows a light member.

According to an embodiment, with reference to FIG. 9, first light member 210 includes a laser 212 that produces force reference laser beam 214; force polarization management 216 produces polarized force reference laser beam 218 in response to receipt of force reference laser beam 214; optical isolator 220 produces isolated output for force reference laser 222 in response to receipt of polarized force reference laser beam 218; force synchronous demodulator 226 produces optomechanical force modulation signal 228 that is communicated to optomechanical reference 100; optical amplifier 224 produces amplified force reference laser beam 232 in response to receipt of isolated output for force reference laser 222 and optomechanical force modulation signal 228; optical isolator 234 produces isolated output for amplified force reference laser beam 236 in response to receipt of amplified force reference laser beam 232; force optical phase modulator 238 produces phase modulated force reference laser beam 246 in response to receipt of isolated output for amplified force reference laser beam 236 and periodic voltage waveform 242; optical circulator 248 produces routing of force reference laser beam into optical cavity, and then back from optical cavity to optical splitter 250 and first laser light 82 in response to receipt of phase modulated force reference laser beam 246, communicates first laser light 82 to first cavity 28A of optomechanical reference 100, and receives first reference light 84 from first cavity 28A of optomechanical reference 100; optical splitter 252 produces first split force reference beam return 254 and second split force reference beam return 256 in response to receipt of routing of force reference laser beam into optical cavity, and then back from optical cavity to optical splitter 250; light measurement sensor 260 produces force light measurement signal 262 in response to receipt of second split force reference beam return 256; electrical phase shifter 268 produces phase shifted force light measurement signal 270 in response to receipt of force light measurement signal 262; demodulator 272 produces demodulated force light measurement signal 274 in response to receipt of phase shifted force light measurement signal 270 and periodic voltage waveform generator 244; force signal feedback electronics 276 produces force measurement feedback signal 278 in response to receipt of demodulated force light measurement signal 274; and laser 212 receives force measurement feedback signal 278 as control feedback from force signal feedback electronics 276.

Figure 10:
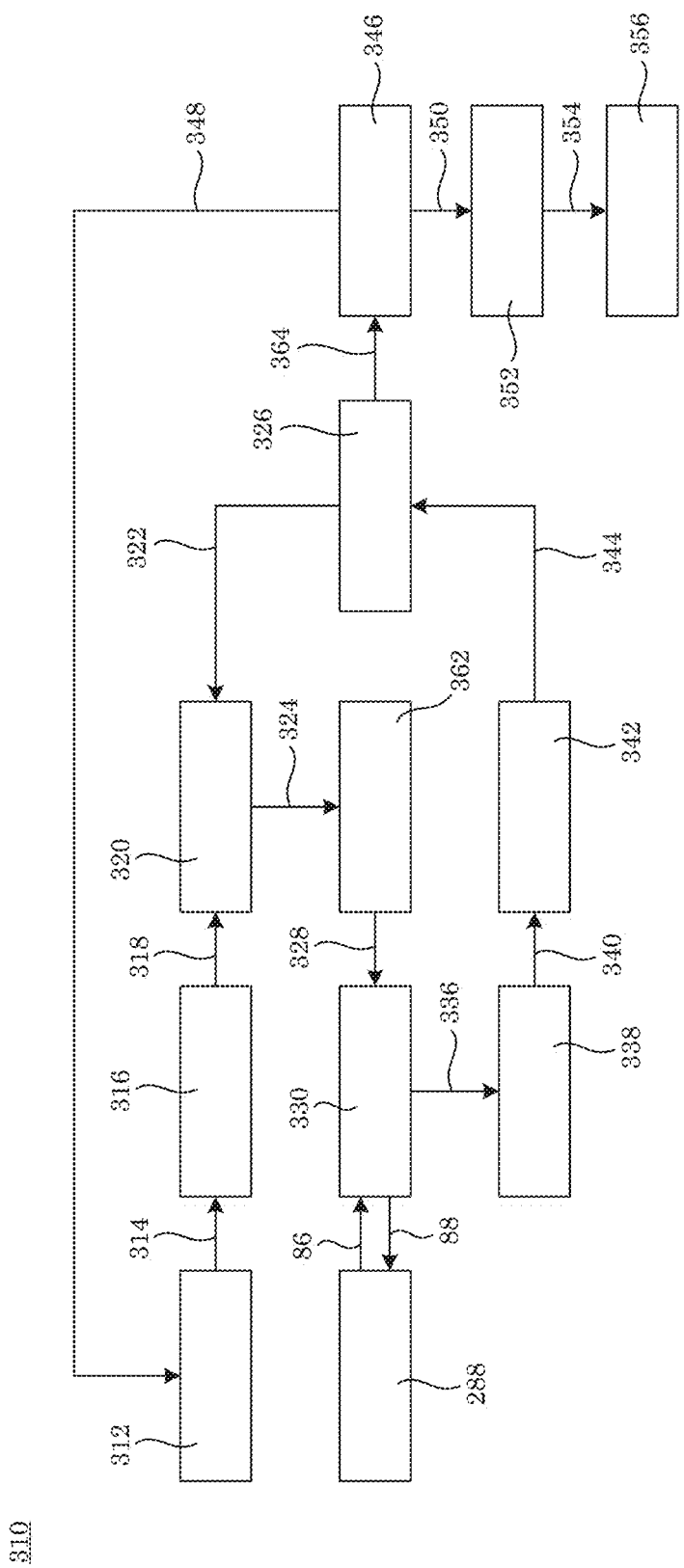
FIG. 10 shows a light member.

According to an embodiment, with reference to FIG. 10, second light member 310 includes displacement laser 312 that produces displacement laser beam 314; displacement polarization management 316 produces polarized displacement measurement laser beam 318 in response to receipt of displacement laser beam 314; displacement optical phase modulator 320 produces phase modulated displacement reference laser beam 324 in response to receipt of polarized displacement measurement laser beam 318 and optomechanical displacement measurement signal 322; optical isolator 362 produces isolated phase modulated displacement reference laser beam 328 in response to receipt of phase modulated displacement reference laser beam 324; optical coupler 330 produces second laser light 86 in response to receipt of isolated phase modulated displacement reference laser beam 328, communicates second laser light 86 to second cavity 28B, receives second reference light 88 from second cavity 28B, and produces routing of displacement reference laser beam into optical cavity, and then back from optical cavity 336; optical splitter 338 produces split displacement measurement laser beam 340 in response to receipt of routing of displacement reference laser beam into optical cavity, and then back from optical cavity 336; displacement light measurement sensor 342 produces displacement measurement signal 344 in response to receipt of split displacement measurement laser beam 340; displacement synchronous demodulator 326 produces optomechanical displacement measurement signal 322 and displacement demodulated signal 364 in response to receipt of displacement measurement signal 344; displacement feedback control 346 produces displacement feedback control signal 348 and force synchronous demodulator B 350 in response to receipt of displacement demodulated signal; synchronous demodulator B 352 produces displacement amplitude signal 354 in response to receipt of force synchronous demodulator B 350; displacement readout 356 produces an amplitude readout in response to receipt of displacement amplitude signal 354; and displacement laser 312 receives displacement feedback control signal 348 as control feedback from displacement feedback control 346.

It is contemplated that laser 212 can include a coherent source of photons with optical elements to produce coherent photons, couple the photons into an optical fiber, change a wavelength of such photons, modulate wavelength, change the power of the beam of photons, control optical isolation, or control polarization.

In first light member 210, force reference laser beam 214 can include a coherent beam of photons or optical fiber to transport photons from laser 212 to force polarization management 216.

In first light member 210, force polarization management 216 can include a coherent beam of photons or optical fiber with optical elements to adjust a polarization state of the coherent beam and can be a device to configure optical fiber into a specific strain state, a device to couple light in and out of an optical fiber, or half waveplates. Moreover, force polarization management 216 produces polarized force reference laser beam 218 that can be a coherent beam of photons in a specified polarization state or optical fiber to transport photons from force polarization management 216 to optical isolator 220.

In first light member 210, optical isolator 220 can include a faraday rotator, polarizers, or a birefringent wedge to prevent optical back reflections from reaching the laser 212 and can be a single unit or a collection of parts. Moreover, optical isolator 220 produces isolated output for force reference laser 222 that can include a coherent beam of photons or optical fiber to transport photons to transport the beam to optical amplifier 224.

In first light member 210, force synchronous demodulator 226 can include a reference signal, a multiplier, and a low pass filter to measure the amplitude of an unknown signal at the frequency of the reference signal. Moreover, force synchronous demodulator 226 produces optomechanical force modulation signal 228 that can include a harmonic electrical signal at a specific amplitude and frequency to provide a modulating signal to optical amplifier 224. Moreover, force synchronous demodulator 226 produces displacement amplitude signal 354 and can include electrical wiring to transport the amplitude readout to displacement readout 356.

In first light member 210, optical amplifier 224 can include optical elements to amplify the power of polarization controlled incident beam of coherent photons. Moreover, optical amplifier 224 can accept optomechanical force modulation signal 228 which uses the amplitude modulating electrical signal to generate and amplitude modulating optical signal and that produces amplified force reference laser beam 232 that can include a coherent beam of photons or optical fiber to transport photons to optical isolator 234.

In first light member 210, optical isolator 234 can include a faraday rotator, polarizers, or a birefringent wedge to prevent optical back reflections from reaching optical amplifier 224. Moreover, optical isolator 234 produces isolated output for amplified force reference laser beam 236 that can include a coherent beam of photons or optical fiber to transport photons to force optical phase modulator 238.

In first light member 210, force optical phase modulator 238 can include optical elements such as an electro-optic element to phase modulate a beam of coherent photons. Moreover, force optical phase modulator 238 produces phase modulated force reference laser beam 246 that can include a coherent beam of photons or optical fiber to transport photons to optical circulator 248.

In first light member 210, optical circulator 248 can include optical elements such as a faraday rotator to separate optical signals that travel in two different directions. Moreover, optical circulator 248 produces routing of force reference laser beam into optical cavity, and then back from optical cavity to optical splitter 250 that can include a coherent beam of photons or optical fiber to transport photons.

In first light member 210, optical splitter 252 can include optical elements such as waveguides to split and optical signal into different components. Moreover, optical splitter 252 and produces first split force reference beam return 254 and second split force reference beam return 256 that can include a coherent beam of photons or optical fiber to transport photons to light measurement sensor 260.

In first light member 210, light measurement sensor 260 can include photoelectric material to convert an optical signal into an electric signal and can be used to measure optical power. Moreover, light measurement sensor 260 produces force light measurement signal 262 that can include an electrical signal and wiring to transport force light measurement signal 262 to electrical phase shifter 268.

In first light member 210, electrical phase shifter 268 can include electrical elements to shift the phase of an incident electrical signal. Moreover, electrical phase shifter 268 produces phase shifted force light measurement signal 270 that can include an electrical signal and wiring to transport phase shifted force light measurement signal 270 to demodulator 272.

In first light member 210, demodulator 272 can include electrical elements such as a signal multiplier and a low pass filter to demodulate phase shifted force light measurement signal 270 at a specified reference frequency. Moreover, demodulator 272 produces demodulated force light measurement signal 274 that can include an electrical signal and wiring to transport demodulated force light measurement signal 274 to force signal feedback electronics 276.

In first light member 210, force signal feedback electronics 276 can include electric elements such as a proportion integral differential (PID) controller to adjust the wavelength of laser 212 such that first cavity 28A is at its resonance wavelength. Moreover, force signal feedback electronics 276 produces force measurement feedback signal 278 that can an electrical signal and wiring to transport and can force measurement feedback signal 278 to laser 212 and can be a single stage PID controller or a multistage PID controller with different signals routed to different components of laser 212.

In second light member 310, displacement laser 312 can include a coherent source of photons with optical elements to produce coherent photons, couple the photons into an optical fiber, change their wavelength, modulate their wavelength, change the power of the beam of photons, control its optical isolation, or control its polarization and can be a single unit or a collection of parts. Moreover, displacement laser 312 produces displacement laser beam 314 that can include a coherent beam of photons or optical fiber to transport photons to displacement polarization management 316.

In second light member 310, displacement polarization management 316 can include can include a coherent beam of photons or optical fiber with optical elements to adjust the beam's polarization state and can be a device to configure optical fiber into a specific strain state, a device to couple light in and out of an optical fiber, or half waveplates. Moreover, displacement polarization management 316 produces polarized displacement measurement laser beam 318 that can include a coherent beam of photons in a specified polarization state or optical fiber to transport photons from displacement polarization management 316 to displacement optical phase modulator 320.

In second light member 310, displacement optical phase modulator 320 can include optical elements such as an electro-optic element to phase modulate a beam of coherent photons. Moreover, displacement optical phase modulator 320 produces phase modulated displacement reference laser beam 324 that can include that can include a coherent beam of photons or optical fiber to transport photons to optical isolator 362.

In second light member 310, optical isolator 362 can include can include a faraday rotator, polarizers, or a birefringent wedge to prevent optical back reflections from reaching displacement laser 312 and can be and can be a single unit or a collection of parts. Moreover, optical isolator 362 produces isolated phase modulated displacement reference laser beam 328 that can include a coherent beam of photons or optical fiber to transport photons to transport the beam to optical coupler 330.

In second light member 310, optical coupler 330 can include optical elements such as waveguides to couple an optical signal into different components. Moreover, optical coupler 330 produces routing of displacement reference laser beam into optical cavity, and then back from optical cavity 336 and can include a coherent beam of photons or optical fiber to transport photons.

In second light member 310, optical splitter 338 can include optical elements such as waveguides to split an optical signal into different components. Moreover, optical splitter 338 produces split displacement measurement laser beam 340 that can include and can include a coherent beam of photons or optical fiber to transport photons to displacement light measurement sensor 342.

In second light member 310, displacement light measurement sensor 342 can include photoelectric material to convert an optical signal into an electric signal and can be used to measure optical power. Moreover, displacement light measurement sensor 342 produces displacement measurement signal 344 that can include an electrical signal and wiring to transport displacement measurement signal 344 to displacement synchronous demodulator 326.

In second light member 310, displacement synchronous demodulator 326 can include a signal multiplier and low pass filter to demodulate displacement measurement signal 344. Moreover, displacement synchronous demodulator 326 produces optomechanical displacement measurement signal 322 that can include can include an electrical signal and wiring to transport optomechanical displacement measurement signal 322 to displacement optical phase modulator 320. Moreover, displacement synchronous demodulator 326 produces displacement demodulated signal 364 can include an electrical signal and wiring to transport displacement demodulated signal 364 to displacement feedback control 346.

In second light member 310, displacement feedback control 346 can include electric elements such as a proportion integral differential (PID) controller to adjust the wavelength of displacement laser 312. Moreover, displacement feedback control 346 produces displacement feedback control signal 348 that can include an electrical signal and wiring to transport displacement feedback control signal 348 to displacement laser 312. Moreover, displacement feedback control 346 produces displacement control readout signal 350 an electrical signal and wiring to transport displacement control readout signal to synchronous demodulator B 352.

In second light member 310, synchronous demodulator B 352 can include a signal multiplier and low pass filter to demodulate force synchronous demodulator B 350 at a specific reference frequency. Moreover, synchronous demodulator B 352 produces displacement amplitude signal 354 that can include an electrical signal and wiring to transport displacement amplitude signal 354 to displacement readout 356.

In second light member 310, displacement readout 356 can include a display and data collection hardware for viewing and recording displacement readout 356.

In an embodiment, a process for making optomechanical reference 100 includes making basal member 20; disposing first stator 23A on basal member 20; disposing second stator 23B on basal member 20; disposing flexure 21 on basal member 20; disposing primary mirrors 30 on flexure 21; and disposing secondary mirrors 32 on stator 23 to form optomechanical reference 100.

Disposing first stator 23A on basal member 20 a fabrication process in which the stator mechanism is created by removal of material from a solid object attached to the basal member.

Disposing second stator 23B on basal member 20 includes a fabrication process in which the stator mechanism is created by removal of material from a solid object attached to the basal member.

Disposing flexure 21 on basal member 20 includes a fabrication process in which the flexure mechanism is created by removal of material from a solid object attached to the basal member.

Disposing primary mirrors 30 on flexure 21 includes placing optical fiber or fibers terminating in mirror surface onto engraved v-grooves on flexure, attaching the optical fiber or fibers to the flexure with adhesive, and removing any portion of the optical fiber overhanging the boundary of the flexure mechanism.

Disposing secondary mirrors 32 on stator 23 includes placing optical fiber or fibers terminating in mirror surface onto engraved v-grooves on flexure, attaching the optical fiber or fibers to the flexure with adhesive, and removing any portion of the optical fiber overhanging the boundary of the flexure mechanism.

Mounting the mirrors on engraved V-grooves which help align the optical cavity interferometer between the frame and floating link 22 to monitor the motion of the flexure mechanism or to provide a radiation pressure reference force. The stators are used as micro-positioning stages to optimize the alignment of the optical cavity. In order to achieve an optimal alignment, appropriate test laser optic, fiber-optic, optoelectronic and signal visualization equipment are used to tune the cavity alignment according to the measured reflected or transmitted signal. Gluing the fiber cables is accomplished using UV-curing epoxy and shining UV light onto the assembly.

Optomechanical reference 100 has numerous beneficial uses, including optomechanical reference metrology. In an embodiment, a process for performing optomechanical reference metrology includes: providing optomechanical reference 100; receiving first laser light 82 by first cavity 28A; reflecting first laser light 82 between first primary mirror 30A and first secondary mirror 32A of first cavity 28A; flexing flexure 21 with respect to first stator 23A in response to reflecting first laser light 82; producing first reference light 84 by first cavity 28A; receiving second laser light 86 by second cavity 28B; reflecting second laser light 86 between second primary mirror 30B and second secondary mirror 32B of second cavity 28B; measuring displacement of floating link 22 with respect to second stator 23B from reflecting second laser light 86; and producing second reference light 88 by second cavity 28B to perform optomechanical reference metrology.

The process for performing optomechanical reference metrology also can include comparing first laser light 82 to first reference light 84 and second laser light 86 to second reference light 88 to produce a comparative signal; and determining a reference force from the comparative signal.

The process for performing optomechanical reference metrology also can include comparing first laser light 82 to first reference light 84 and second laser light 86 to second reference light 88 to produce a comparative signal; and determining a reference displacement from the comparative signal.

The process for performing optomechanical reference metrology also can include comparing first laser light 82 to first reference light 84 and second laser light 86 to second reference light 88 to produce a comparative signal; and determining a reference mass from the comparative signal.

The process for performing optomechanical reference metrology also can include comparing first laser light 82 to first reference light 84 and second laser light 86 to second reference light 88 to produce a comparative signal; and determining a reference stiffness from the comparative signal.

The process of performing optomechanical reference metrology can also include measurement of the thermomechanical motion of flexure 21 to provide an independent measurement of the stiffness of flexure 21.

Also, the process of performing optomechanical reference metrology can be used to calibrate an external device as a sensor for force, mass, or stiffness.

In the process for performing optomechanical reference metrology, receiving first laser light 82 by first cavity 28A includes propagation of laser light into optical waveguide 34.

In the process for performing optomechanical reference metrology, reflecting first laser light 82 between first primary mirror 30A and first secondary mirror 32A of first cavity 28A includes reflection first laser light 82 from first primary mirror 30A to first secondary mirror 32A.

In the process for performing optomechanical reference metrology, flexing flexure 21 with respect to first stator 23A in response to reflecting first laser light 82 includes deformation of flexural members 24A and 24B in response to the radiation pressure from reflection of laser light within cavity 28A.

In the process for performing optomechanical reference metrology, producing first reference light 84 by first cavity 28A includes collection first reference light 84.

In the process for performing optomechanical reference metrology, receiving second laser light 86 by second cavity 28B includes propagation of laser light into optical waveguide 34.

In the process for performing optomechanical reference metrology, reflecting second laser light 86 between second primary mirror 30B and second secondary mirror 32B of second cavity 28B includes reflection of first laser light 82 from first primary mirror 30A and first secondary mirror 32A.

In the process for performing optomechanical reference metrology, flexing flexure 21 with respect to second stator 23B in response to reflecting second laser light 86 includes measurement of deflection of floating link 22.

In the process for performing optomechanical reference metrology, producing second reference light 88 by second cavity 28B includes propagation of laser light into optical waveguide 34.

In the process for performing optomechanical reference metrology, comparing first laser light 82 to first reference light 84 to produce a comparative signal by mixing the laser light to generate optical interference. Determining a reference force from the comparative signal includes detecting the mixed laser light intensity with photodetector 258 or 260. The intensity of the mixed laser light provides data of an optical phase of first laser light 82 relative to first reference light 84. The optical phase is used to determine and control an amount of optical power circulating in first cavity 28A. The radiation pressure force acting on primary mirror 30A is determined by the amount of optical power circulating in cavity 28A.

In the process for performing optomechanical reference metrology, comparing second laser light 86 to second reference light 88 to produce a comparative signal by mixing the laser light to generate optical interference. Determining a reference displacement from the comparative signal includes detecting the mixed laser light intensity with photodetector 342. The intensity of the mixed laser light yields information about the optical phase of second laser light 86 relative to second reference light 88. This phase information allows for determination and control of the displacement of floating link 22.

Measurement of reference force and reference displacement described provides determination of a stiffness of optomechanical reference 100 as a ratio of reference force to reference displacement.

Measurement of reference displacement can be used to determine the resonant frequencies of optomechanical reference 100. The resonant frequencies of optomechanical reference 100 shift in response to the addition of mass. The shift in resonant frequency combined with the stiffness provides determination of the change in mass of the floating link 22.

Measurement of reference displacement is used to determinate the thermomechanical motion of floating link 22 in an absence of externally applied force. The thermomechanical motion is used to determine the stiffness of the optomechanical reference 100 and to provide a check of other quantities.

Optomechanical reference 100 has numerous advantageous and beneficial properties. In an aspect, optomechanical reference 100 provides stable calibration by comparison to optical standards.

Optomechanical reference 100 advantageously and unexpectedly is light-weight and compact to provide metrological measurements and overcomes a hefty weight of conventional devices that can weigh several kilograms and that can be a size of a backpack, e.g., 270 cm$^3$. Beneficially, optomechanical reference 100 is highly compact and light with an acceleration noise floor on the order of $10^{-10}$ m s$^{-2}$ Hz$^{-1/2}$. A total weight can be about 30 grams, including optical components such as an optical interferometer that can be constructed out of compact optics to provide in interferometer links from 1 μm to 2 cm and that involves fiber-optics.

The articles and processes herein are illustrated further by the following Example, which is non-limiting.

EXAMPLE

Figure 11:
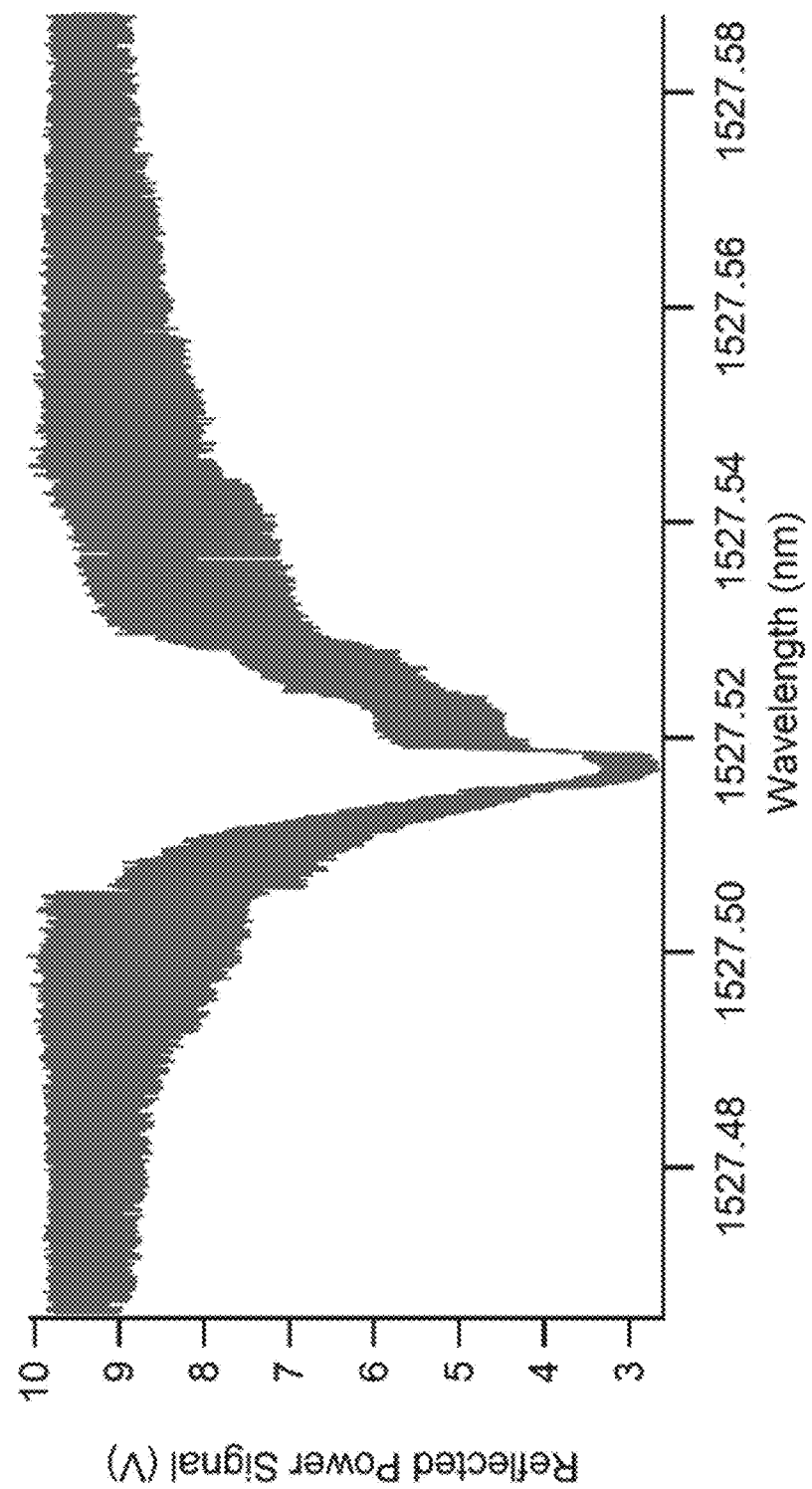
FIG. 11 shows a graph of reflected power signal versus wavelength.
Figure 12:
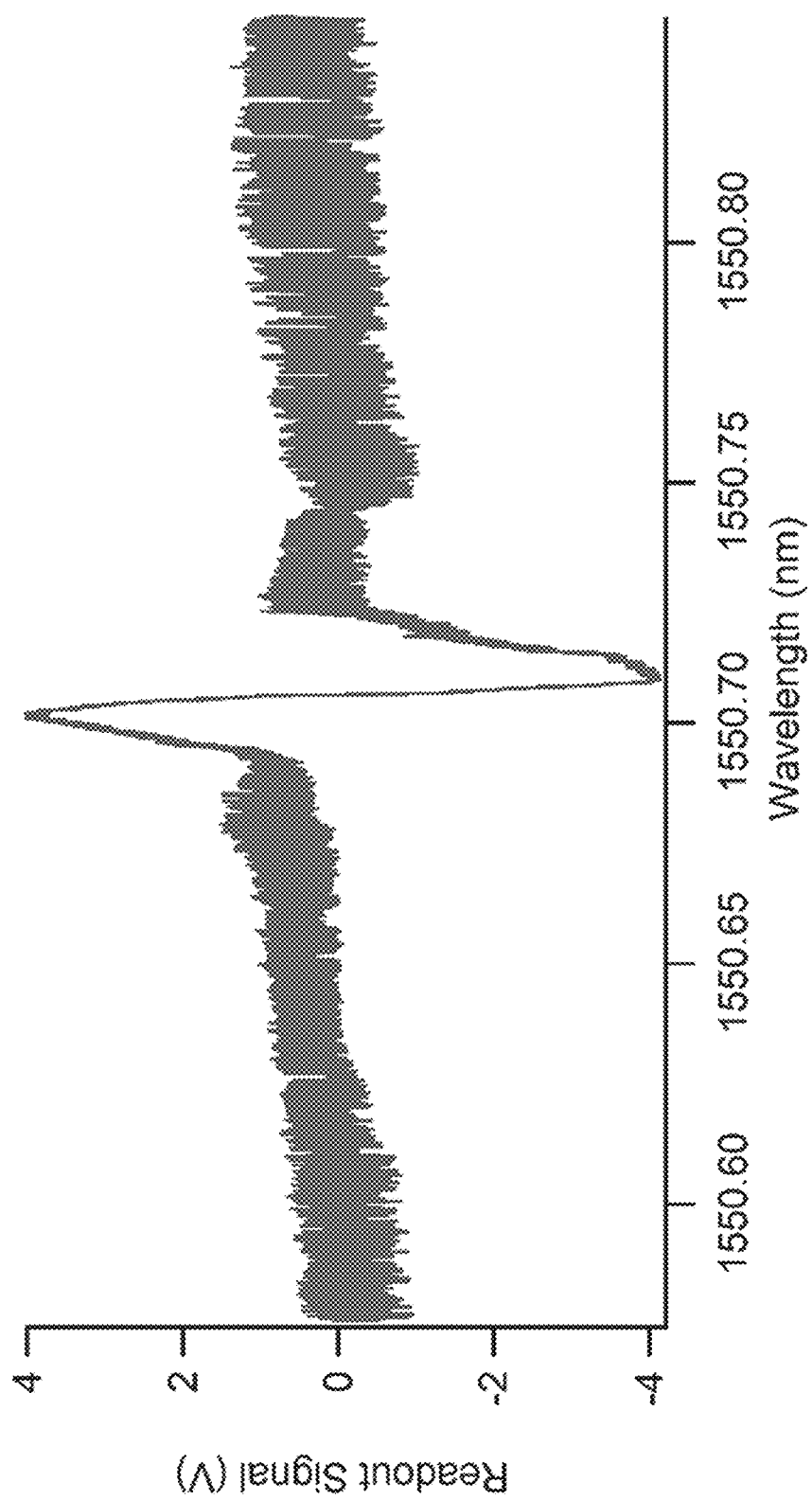
FIG. 12 shows a graph of readout signal versus wavelength.

Laser 212 or 312 wavelength is scanned to locate a minimum in reflected light signal shown in FIG. 11 as detected by photodiode 258, 260 or photodiode 342, and recorded by a data acquisition system. This corresponds to the optical resonance of optical cavity 28A or 28B. From the reflected light signal collected by the data acquisition system, a finesse and free spectral range of the optical cavity is calculated. The wavelength scan was accompanied by modulation of the optical phase of the isolated output for amplified force reference laser beam 236 or the polarized displacement measurement laser beam 318. Demodulation of the light signal detected by photodiode 258, 260, or 342 produces a differential signal as shown in FIG. 12. This differential signal is used to calibrate the amplitude readout 356 to measure displacement of the floating link 22. Laser 212 or 312 wavelength is controlled based on feedback control 276 or 346 to maintain a specific setpoint in the differential signal shown in FIG. 12.

Figure 13:
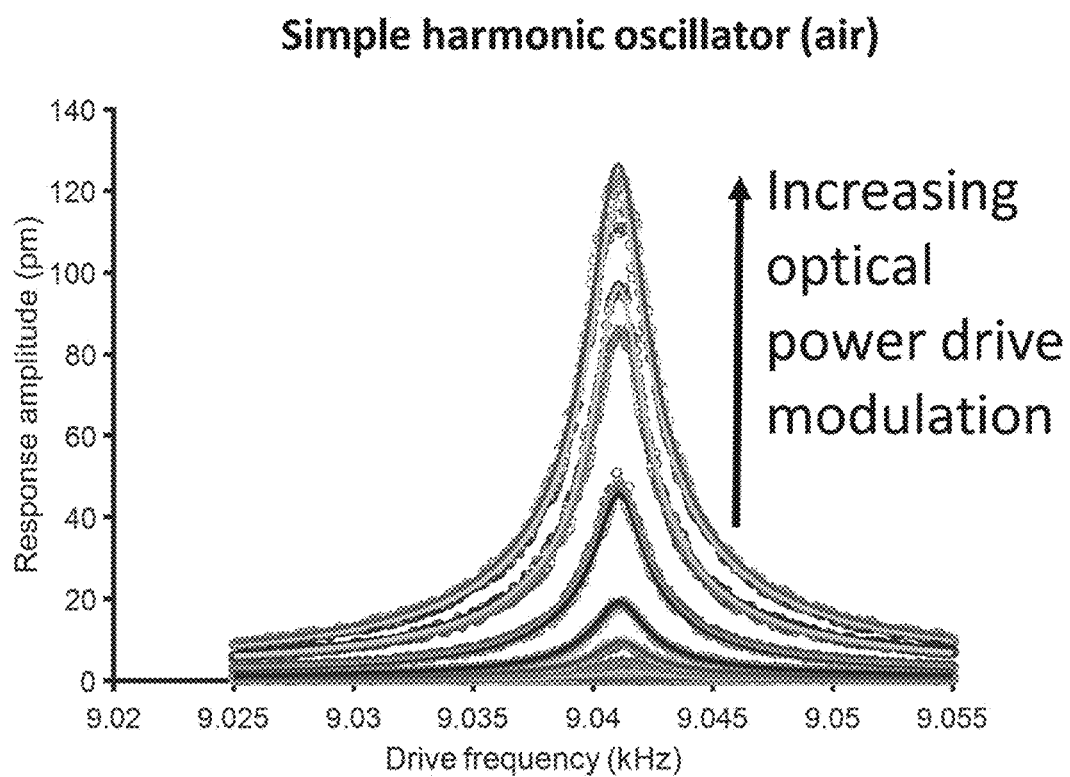
FIG. 13 shows a graph of response amplitude versus drive frequency.

The bandwidth of feedback control 276 or 346 is set bypass a modulation frequency. The intensity of the laser light propagating to optical cavity 28A is controlled by optical amplifier 224. Changing the intensity of the laser light changes the radiation pressure force acting on 30 A, causing motion of floating link 22. The change in the resulting amplitude of motion of the floating link 22 in response to increasing periodic modulation of the laser light intensity is shown in FIG. 13 for a periodic modulation near the first resonant frequency of the optomechanical force reference.

Figure 14:
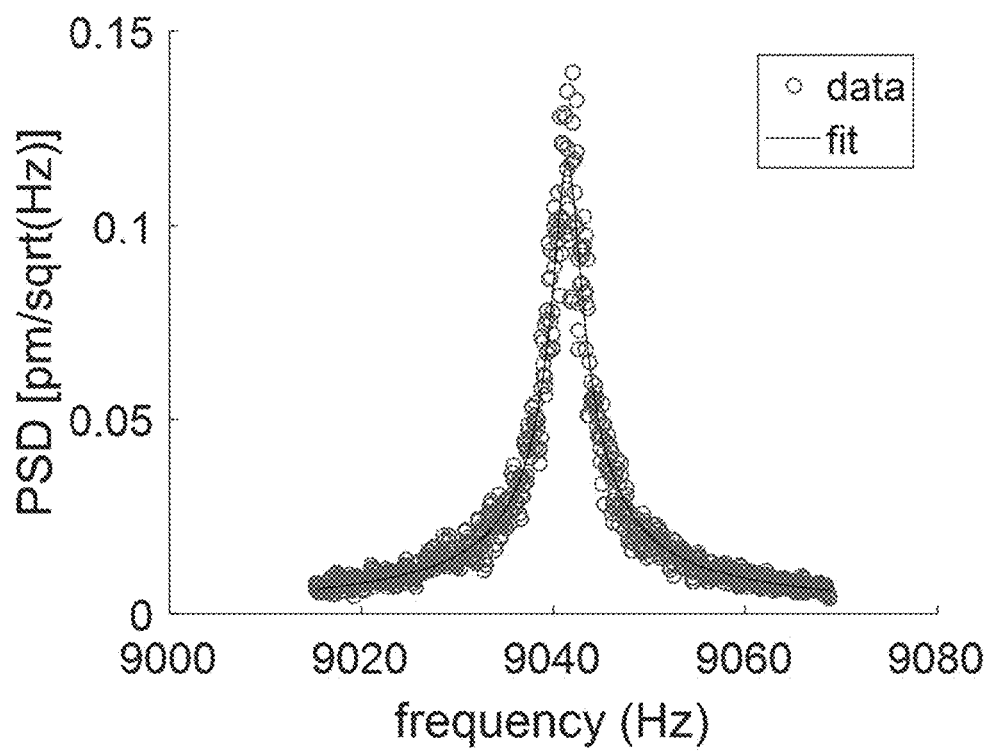
FIG. 14 shows a power spectral density (PSD) versus frequency.

The motion of floating link 22 can also be monitored in the absence of modulated laser light intensity as is shown in FIG. 14. In this case, the thermomechanical motion of the floating link can be used to determine the stiffness of the optomechanical force reference flexure 21, providing a means to verity the radiation pressure force measurement.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may.

Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An optomechanical reference comprising:
    a basal member;
    a flexure disposed on the basal member and comprising:
        a floating link disposed on the basal member;
        a first flexural member interposed between the basal member and the floating link; and
        a second flexural member interposed between the basal member and the floating link such that:
            the floating link is moveably disposed on the basal member via flexing of the first flexural member and the second flexural member, and
            the first flexural member and the second flexural member are spaced apart and in mechanical communication by the floating link;
    a first stator disposed on the basal member and opposing the flexure such that:
        the first stator is spaced apart from the flexure, and
        the first stator is subject to displacement when the basal member is displaced;
    a second stator disposed on the basal member and opposing the flexure such that:
        the second stator is spaced apart from the flexure, and
        the second stator is subject to displacement when the basal member is displaced;

a first cavity comprising:
    a first primary mirror disposed on the flexure;
    a first secondary mirror disposed on the first stator and in optical communication with the first primary mirror;
    a first optical coupler in optical communication with the first secondary mirror and that provides a first laser light to the first cavity; and
    a first cavity length comprising a first distance between the first primary mirror and the first secondary mirror; and
a second cavity comprising:
    a second primary mirror disposed on the flexure;
    a second secondary mirror disposed on the second stator and in optical communication with the second primary mirror;
    a second optical coupler in optical communication with the first secondary mirror and that provides a second laser light to the second cavity; and
    a second cavity length comprising a second distance between the second primary mirror and the second secondary mirror.

2. The optomechanical reference of claim 1, wherein the flexural member comprises a leaf spring.

3. The optomechanical reference of claim 1, further comprising a piezoelectric member disposed on the first stator.

4. The optomechanical reference of claim 1, further comprising a piezoelectric member disposed on the second stator.

5. The optomechanical reference of claim 1, further comprising:
    an armature disposed on the basal member,
    wherein the first stator and second stator are disposed on the armature.

6. The optomechanical reference of claim 5, wherein the first primary mirror and the second primary mirror are disposed on a same surface of the flexure.

7. The optomechanical reference of claim 1, further comprising:
    a first armature disposed on the basal member,
    wherein the first stator is disposed on the first armature.

8. The optomechanical reference of claim 7, further comprising:
    a second armature disposed on the basal member,
    wherein the second stator is disposed on the second armature.

9. The optomechanical reference of claim 8, wherein the flexure is interposed between the first stator and the second stator.

10. A process for performing optomechanical reference metrology, the process comprising:
    providing an optomechanical reference of claim 1;
    receiving the first laser light by the first cavity;
    reflecting the first laser light between the first primary mirror and the first secondary mirror of the first cavity;
    flexing the flexure with respect to the first stator in response to the reflecting the first laser light;
    producing first reference light by the first cavity;
    receiving the second laser light by the second cavity;
    reflecting the second laser light between the second primary mirror and the second secondary mirror of the second cavity;
    flexing the flexure with respect to the second stator in response to the reflecting the second laser light; and
    producing second reference light by the second cavity to perform optomechanical reference metrology.

11. The process of claim 10, further comprising:
    comparing the first reference light to the second reference to produce a comparative signal; and
    determining a reference force from the comparative signal.

12. The process of claim 10, further comprising:
    comparing the first reference light to the second reference to produce a comparative signal; and
    determining a reference mass from the comparative signal.

13. The process of claim 10, further comprising:
    comparing the first reference light to the second reference to produce a comparative signal; and
    determining a spring stiffness from the comparative signal.

* * * * *